(12) United States Patent
Clark

(10) Patent No.: US 6,535,819 B1
(45) Date of Patent: Mar. 18, 2003

(54) OPTIMAL DISSIMILARITY METHOD FOR CHOOSING DISTINCTIVE ITEMS OF INFORMATION FROM A LARGE BODY OF INFORMATION

(75) Inventor: Robert D. Clark, St. Louis, MO (US)

(73) Assignee: Tripos, Inc., St. Louis, MO (US)

( * ) Notice: Subject to any disclaimer, the term of this patent is extended or adjusted under 35 U.S.C. 154(b) by 0 days.

(21) Appl. No.: 09/059,017

(22) Filed: Apr. 13, 1998

Related U.S. Application Data

(63) Continuation-in-part of application No. 08/833,955, filed on Apr. 11, 1997, now abandoned.

(51) Int. Cl.$^7$ .............................. G06F 19/00; C12Q 1/68
(52) U.S. Cl. .............................................. 702/19; 435/6
(58) Field of Search ........................ 435/7.1, 6; 702/19, 702/20, 21

(56) References Cited

PUBLICATIONS

Higgs et al., "Experimental Design for Selecting Molecules from Large Chemical Databases" J. Chem. Inf. Comput. Sci. vol. 37, pp. 861–870, 1997.*

* cited by examiner

*Primary Examiner*—John S. Brusca
(74) *Attorney, Agent, or Firm*—Laurence Weinberger

(57) ABSTRACT

The method of this invention identifies distinctive items of information from a larger body of information on the basis of similarities or dissimilarities among the items and achieves a significant increase in speed as well as the ability to balance the representativeness and diversity among the identified items by applying selection criteria to randomly chosen subsamples of all the information. The method is illustrated with reference to the compound selection requirements of medicinal chemists. Compound selection methods currently available to chemists are based on maximum or minimum dissimilarity selection or on hierarchical clustering. The method of the invention is more general and incorporates maximum and minimum dissimilarity-based selection as special cases. In addition, the number of iterations required to select the items is a multiple of the group size which, at its greatest, is approximately the square root of the population size. Thus, the selection method runs much faster than the methods of the prior art. Further, by adjusting the subsample size parameter K, it is possible to control the balance between representativeness and diversity in the compounds selected. In addition, the method can mimic the distributional properties of selections based on hierarchical clustering and, at least in some cases, improve upon them.

17 Claims, 14 Drawing Sheets

OPTIMAL DISSIMILARITY METHOD FOR CHOOSING DISTINCTIVE ITEMS OF INFORMATION FROM A LARGE BODY OF INFORMATION

This patent document is a continuation-in-part of U.S. patent application Ser. No. 08/833,955 filed Apr. 11, 1997 now abandoned. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

A method is presented which identifies distinctive items of information from a larger body of information on the basis of similarities or dissimilarities among the items. More specifically, the method achieves a significant increase in speed as well as the ability to balance the representativeness and diversity among the identified items by applying selection criteria to randomly chosen subsamples of all the information.

2. Description of Background Art

Most disciplines from economics to chemistry are benefiting from the ability of the modern computer to store and retrieve vast amounts of data. While the chore of actually handling the data has been reduced, the ability to gather, store, and operate with the enormous amount of data has, in itself, created new problems. In particular, in some cases the amount of data has become so vast that it is difficult to comprehend the range of data, much less to understand and derive meaningful information from it. To address this problem, attempts have been made in the prior art to find ways to meaningfully group or abstract some structure from the information.

For instance, in many situations it is useful to use a stratified sampling procedure for getting aggregate information about a population within which different groups cost different amounts to survey, or whose response have different meanings to the questioner, etc. However, while the stratified sampling approach is very efficient, to use it one must be able to quickly get information about each cluster within the population, and be able to select representative people to poll. The method of this invention permits the rapid evaluation of the demographic profiles in such a situation to see how many people in a random sample are "closest" to each selectee. Small, but information profitable target groups can then be surveyed in this way.

The approach of this invention could also aid in the design of clinical trials. It often happens that drugs tested in a small random sample fail later because of severe adverse reactions in a small subpopulation. Using the method of this invention, a selection based on medical and family history could produce a more useful early phase test population. The following discussion of the method of this invention is presented in terms useful to medicinal chemists who are concerned with identifying subpopulations of chemical compounds. However, as can be seen from the brief examples above, the method of the invention is general and can equally well be applied to other fields by those skilled in the art. The generality of the method is readily appreciated if for the term "compound" used in this disclosure, the term "data element" is substituted. Brief examples of other specific applications of the methodology of the invention are set out at the end of the disclosure.

The advent of combinatorial chemistry and high throughput screening has made the ability to identify "good" subsets in large libraries of compounds very important, whether the libraries in question have actually been synthesized or exist as assemblies of virtual molecular representations in a computer. One kind of a good subset is one which contains members which represent the chemical diversity inherent in the entire library while at the same time not containing more members than are necessary to sample the inherent diversity. This desire for a good subset is driven by the fact that these libraries can contain an enormous number of compounds which, if every single compound were tested, would be extremely costly in terms of money, time, and resources to individually evaluate. Essentially, what is desired is a subset of a size which is reasonable to test. Clearly, good subsets can be generated based upon other criteria as well, such as ease of synthesis or lowest cost. Traditionally such subsets have been created by expert systems—i.e., having a medicinal or pesticide chemist select compounds manually based on a series 2D structures. This approach is labor-intensive and is dependent on the expert used. Moreover, it is neither routinely practical nor very good for more than 300–1000 compounds, and then only when the library in question includes one or more homologous series. In the prior art, currently available alternative approaches for selection include maximum dissimilarity selection, minimum dissimilarity selection, and hierarchical clustering, among others[1]. Each of the available methods can be effective, but each has some intrinsic limitations.

Maximum Dissimilarity: The methods currently most often used for selecting compounds focus on maximizing the diversity of the selected subset with respect to the set as a whole using a descriptor (metric) which characterizes the members of the set and an associated (dis)similarity measure[1-3]. The basic approach is straightforward, and utilizes as parameters a minimum acceptable dissimilarity (redundancy) threshold R and a maximum selected subset size $M_{max}$. The approach is essentially as follows:

1. Select a compound at random from the dataset of interest, add it to the selection subset, and create a pool of candidate compounds out of the remainder of the dataset.
2. Examine the pool of candidates, and, using the characterizing measure (metric), identify the candidate which is most dissimilar to those which have already been selected.
3. Determine whether the dissimilarity of the most dissimilar candidate is less than R (redundancy test). If it is less than R, stop. If it is not less than R, add that candidate to the selection set and remove it from the pool of candidates.
4. If the compound to be selected in this step is the third compound being selected, after its selection return the first two selections to the pool of candidate compounds. (The first selection was chosen randomly, and the second selection is strongly biased by the first. Transferring them back into the candidate pool reduces the effect of the initial random selection.)
5. If the desired subset size M has been reached, stop.
6. If there are no more candidates in the pool, stop. If there are more candidates in the pool, go back to step 2.

A related method developed by Agrafiotis works by comparing evolving subsets to maximize the diversity across the entire set[4]. Maximally diverse subsets are, by definition, biased towards inclusion of outliers; i.e., those candidates most dissimilar from the group as a whole. In some situations, this is very useful property, but medicinal chemists tend to avoid outliers in making their own selections because they may not "look like" drugs. In some cases, outliers in corporate databases are outliers for good reason—difficulty of synthesis or toxicity, for example—which reduces their value as potential leads. Moreover, a maximally diverse subset may not be adequately representative of the biochemical diversity in a dataset.

One justification in drug research for maximizing diversity is based on experimental design considerations commonly employed for analyzing quantitative structure/activity relationships (QSARs),[5] where outliers are important because they have the greatest weight. The libraries from which subsets are to be selected are usually much more diverse and much larger in size than those used for QSAR, however. In such a situation, outliers loose their statistical leverage because it may no longer be possible to use the QSAR approach to adequately approximate biochemical responses as linear or quadratic functions of the descriptors (metrics) being used.

Minimum Dissimilarity: Recently, Robert Pearlman et al. introduced an alternative approach to compound selection (the "elimination method" in DiverseSolutions[6]) which can be characterized as minimum dissimilarity selection. The approach takes the same two parameters as maximum dissimilarity selection—a minimum dissimilarity threshold R and $M_{max}$, the maximum number of compounds to select—but applies them differently as follows:

1. Select a compound at random from the dataset of interest, add it to the selection set, and create a pool of candidate compounds out of the remainder of the dataset.
2. Examine the pool of candidates, and, using the characterizing measure (metric), remove any for which the dissimilarity to the most recent selection is less than R.
3. If there are no more candidates in the pool, stop.
4. Select a compound at random from the pool of candidates.
5. If the desired subset size M has been reached, stop.
6. Go back to step 2.

Notice that in each iteration, the similarity test (step 2) is applied only with respect to the most recent compound selected at that iteration. This limits the method to pairwise measures of dissimilarity and can not be used with measures between single compounds and a set of compounds. As Holliday and Willett have pointed out, the definition of set-wise dissimilarity can radically affect the outcome of a dissimilarity-based selection method,[3] just as the linkage method used can affect the outcome of hierarchical clustering.[7,8]

Minimum dissimilarity selection tends to be order dependent[1]; i.e., the members included will be dependent on the initial random selections. This can be alleviated by setting $M_{max}$ very high, so that the method runs to exhaustion; i.e., runs out of candidates before M is reached [stops at step 3]. For most datasets, doing so with an empirically justified value for R (e.g., 0.15–0.2 for Tanimoto dissimilarity of 2D fingerprints[9,10]) will return an undesirably large number of selections. Typically, it is necessary to repeat the minimum dissimilarity selection several times on the same dataset in order to find a value of R which will yield the desired number of selections when minimum dissimilarity is run to exhaustion.

If a reasonable value of $M_{max}$ and a neighborhood[10] radius R are used, the minimum dissimilarity method will return a subset similar to one chosen by random selection, where the only difference is that there will be no redundant selections, as defined by R. Such a selection will be representative but may not be diverse enough to satisfy some chemists.

Hierarchical Clustering: In agglomerative hierarchical clustering, the most similar pair of clusters are consolidated at each level, starting from one singleton cluster for each compound in the set. Selecting from clusters obtained using Ward's or complete-linkage methods[1,8] returns subsets which are both representative and diverse, in that each compound is represented by some neighbor and the representatives are distributed across the full breadth of the dataset. Medicinal chemists generally find selections based on hierarchical clustering intuitively appealing and natural, especially after they have eliminated "oddball" clusters and singleton compounds from the selection list. Indeed, they sometimes make their own selections by manually clustering structures. By examining the dissimilarity between the most similar clusters at each step, one can identify the most "natural" level of clustering near the number of compounds one wishes to select—i.e., levels at which the last clusters consolidated were substantially more similar than any remaining clusters are to each other.

Hierarchical clustering is not always a practical option, however. The speed of the classical technique decreases with the cube of the size N of the dataset,[1,8] and so becomes slow for large libraries. In addition, computer memory requirements generally restrict direct applications to relatively small datasets ($\leq 2000$ compounds). Faster approaches, including reciprocal nearest neighbors (RNN),[8] are available which relieve the memory limitations and can usually reduce scaling problems dramatically.[1] However, even in the best case, the speed is inversely proportional to $N^2$. Unfortunately, the scaling benefits can only be fully realized when centroids are well-defined and well-behaved in the metric space being explored, which is not the case for some important metrics of interest—in particular, for Tanimoto similarities between 2D fingerprints.[9,10]

Definitions

N shall mean the entire set of elements contained in a dataset from which it is desired to select a subset.

M shall mean the size of the subset of elements which it is desired to select.

R shall mean an exclusion criterion chosen by the user. One example of such a criterion is a minimum dissimilarity threshold between the data elements.

K shall mean a subsample size chosen by the user.

SUMMARY OF THE INVENTION

The method of this invention addresses the problem of how to select from a very large dataset of information, a smaller subset for detailed analysis and/or evaluation which reflects the full range of information contained in the large dataset. The present method significantly improves on the methods available in the prior art in two significant ways. First, it is possible to adjust the balance for a data subset between how representative the selected subset is and how diverse it is. Second, the method achieves the desired selection much faster than any comparable method. In particular, while the number of fundamental steps to obtain a subset of a given size in prior art methods are multiples of the size of the dataset N or powers of $N^x$, it has been discovered that, with the method of this invention, the number of steps required is a multiple of M which, at its greatest, is approximately the square root of N, $\sqrt{N}$.

In prior art selection methods large datasets are examined as a whole. In the method of this invention a subsample K of the entire dataset size N is defined and examined. The method of this invention is more general than those of the prior art, and, in fact, reduces as limiting cases to the minimum and maximum dissimilarity methods of the prior art for values of K=1 and K=N. The tradeoff between how representative or how diverse the selected subset is may be varied by the user by selecting intermediate values of K.

DESCRIPTION OF THE PREFERRED EMBODIMENT

Figure 1:
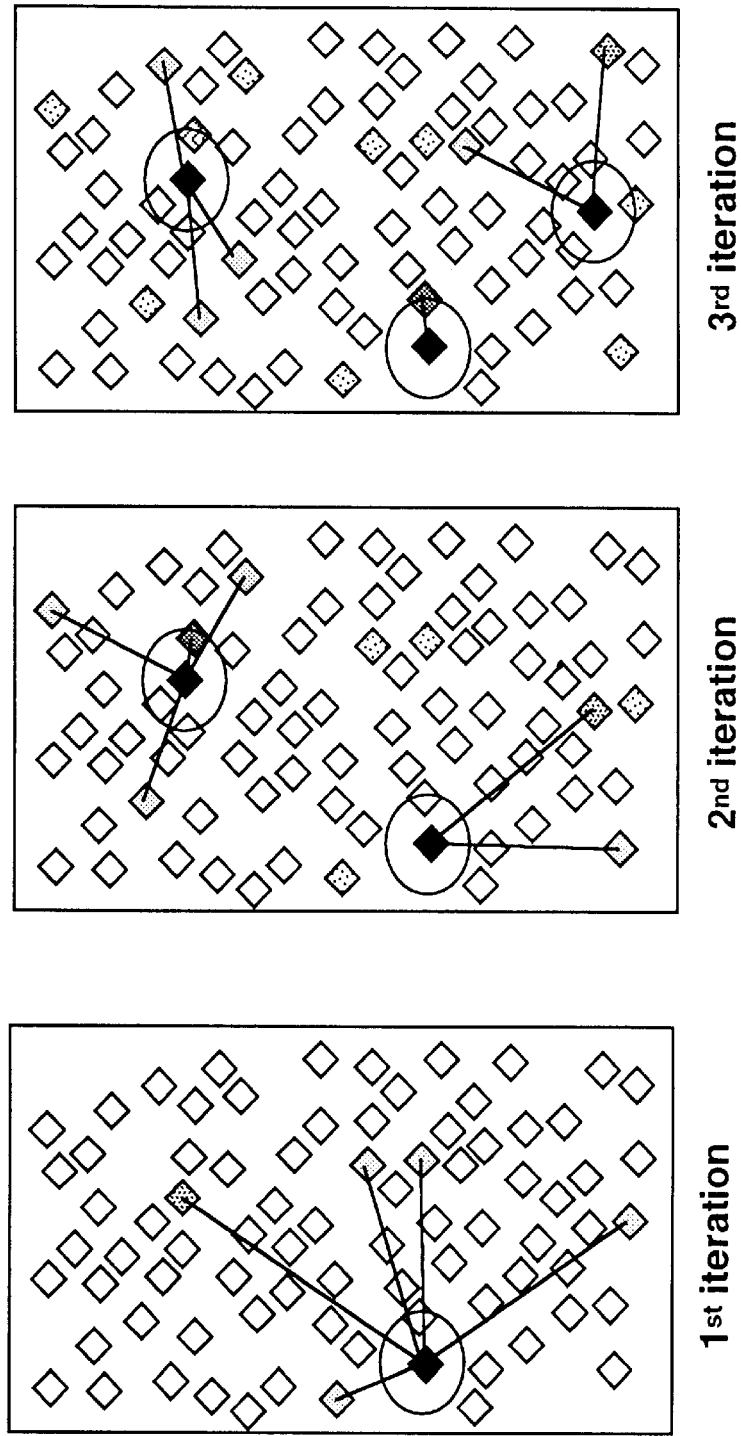
FIG. 1 diagrammatically shows the compounds chosen at each of the first three iterations of a selection performed by the method of this invention (R=6 mm (original scale), K=5, $M_{max} \geq 3$). Symbols representing compounds which have already been selected are filled in solid. The circles around each solid symbol show the minimum dissimilarity radius R; dark hash symbols indicate compounds examined at each iteration which are excluded as too similar to those which have already been selected. Stippled symbols indicate candidates in the recycling bin, i.e., which have already been considered for selection once.

Holliday and Willett have pointed out[3] that their own[11] and other[2] dissimilarity-based selection methods were actually specific manifestations of a more general, unified method, and in particular, they addressed the question of what similarity meant when comparing one compound to a group of compounds. Lance and Williams[7] have done much the same analysis for hierarchical clustering. In a similar way, maximum and minimum dissimilarity selection can be reformulated as limiting cases of a single, more general method, the "OptiSim" method of this invention. The generalization entails introduction of a parameter K which defines a subsample size at each iteration. The method can be outlined as follows:

1. Select a compound at random from the dataset of interest, add it to the selection set, and create a pool of candidate compounds out of the remainder of the dataset. Create an empty recycling bin.
2. Randomly select a subsample set of K compounds (or all remaining) from the candidate pool. If necessary, transfer compounds from the recycling bin to the candidate pool and randomly select a sufficient number of compounds (if possible) to complete a subsample of size K.
3. Determine whether any of the compounds in the subsample set have a dissimilarity less than R with respect those compounds already selected. (In the case of the first pass, this will only be the initially randomly selected compound.) Remove any such compounds from the subsample and replace them with other compounds from the candidate pool.
4. If the candidate pool is exhausted, remove all compounds from the recycling bin and put them back into the candidate pool.
5. Repeat step 3 until the subsample includes K compounds at least R dissimilar to those already selected or until the candidate pool is exhausted.
6. If the subsample is empty, stop.
7. If the subsample is not empty, examine the subsample, and identify a compound maximally dissimilar to those already selected.
8. Add the compound identified in step 7 to the selection set and remove it from the subsample.
9. Put those compounds in the subsample which were not selected into the recycling bin.
10. If the desired selected subset size M has been reached, stop. If the desired selected subset size M has not been reached, return to step 2.

A preferred alternative formulation of the method can be set out as follows:

1. Select a compound at random from the dataset of interest, add it to the selection set, and create a pool of candidate compounds out of the remainder of the dataset. Create an empty recycling bin.
2. Randomly choose another compound from the dataset and determine if it has a dissimilarity less than R with respect to those compounds already selected for the selection set. If it does not have a dissimilarity less than R, place it in the subsample.

3. Repeat step 2 until the subsample includes K compounds at least R dissimilar to those already selected or until the candidate pool is exhausted.
4. If the candidate pool is exhausted but the recycling bin is not exhausted, remove all compounds from the recycling bin and put them back into the candidate pool.
5. If the candidate pool is not exhausted and there are fewer than K compounds in the subsample, go to step 2.
6. If the subsample is empty, stop.
7. If the subsample is not empty, examine the subsample and identify a compound maximally dissimilar to those already selected.
8. Add the compound identified in step 7 to the selection set and remove it from the subsample.
9. Put those compounds in the subsample, which were not added to the selection set, into the recycling bin.
10. If the desired selected subset size M has been reached, stop. If the desired selected subset size M has not been reached, return to step 2.

Figure 7:
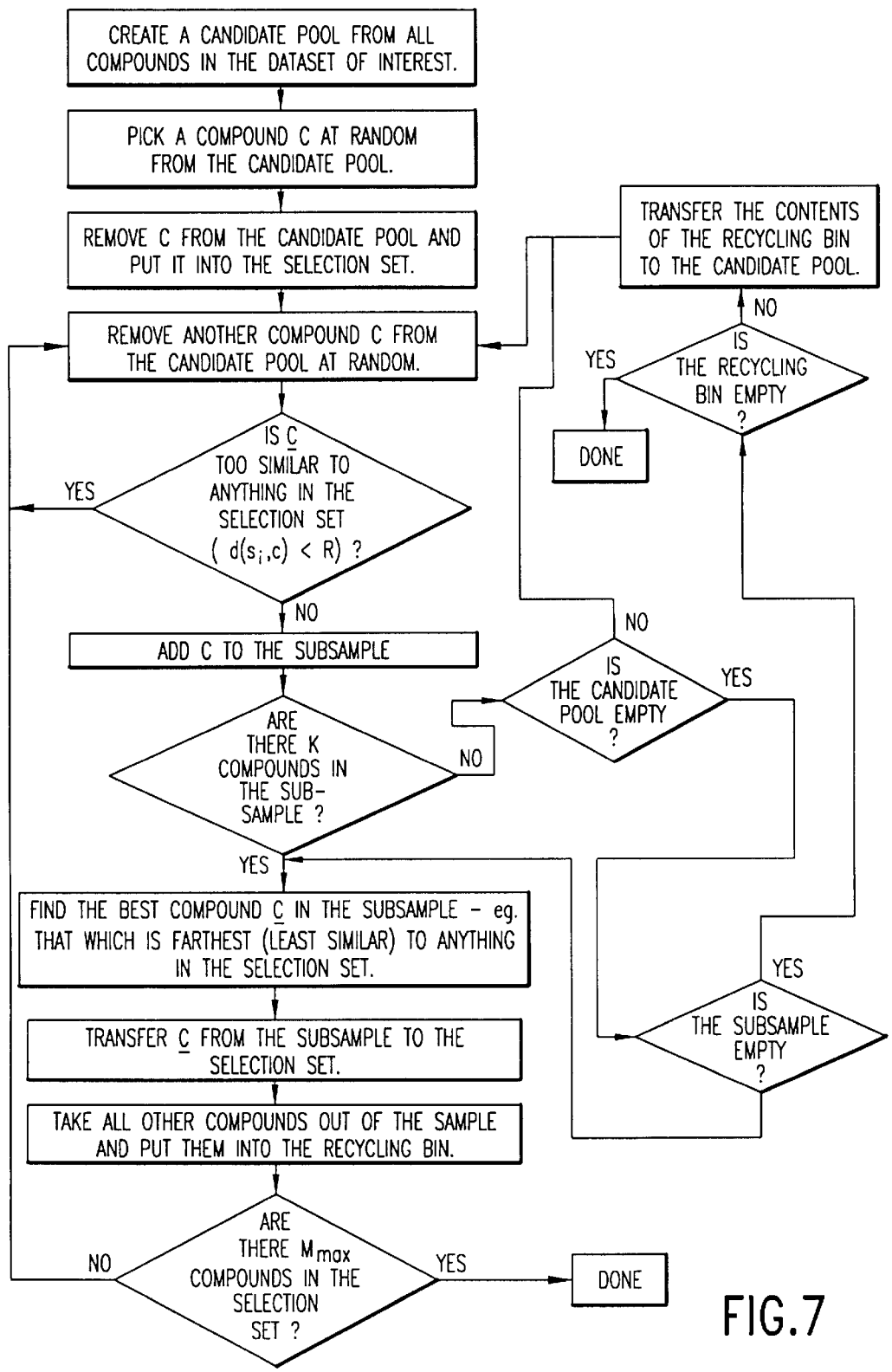
FIG. 7 is a diagrammatic flow sheet of the invention.

FIG. 7 shows the method of this invention set out in flowsheet format.

The results of the application of the first formulation of the method for three iterations are illustrated schematically in FIG. 1, where filled in symbols indicate selected compounds.

Clearly, the maximum and minimum dissimilarity selection methods can be seen simply as extreme instances of this Optimal Dissimilarity Selection approach[12]—OptiSim, for short. For maximum dissimilarity, K is effectively N, the number of elements in the dataset: all compounds are considered as candidates at each step. The only substantive difference from the prior art maximum similarity method is that the first two selections are not dropped (step 4 in the maximum dissimilarity approach), so the selections obtained are slightly more representative and less diverse than would be the case for the original method.

For minimum dissimilarity, K is simply 1. In addition, the similarity test (step 3) is applied to each candidate with respect to all elements which have already been selected. This method broadens the range of dissimilarity measures which can be used over the version of the minimum dissimilarity method described above.

An important aspect of the present invention is that, by choosing an intermediate value of K, it is possible to strike a balance along the continuum between the diversity of the maximum dissimilarity approach and the representativeness of the minimum dissimilarity approach. As shown below, it turns out that one can mimic selection based on hierarchical clustering as well. Thus, the method of this invention is more general than prior art approaches and, when desired, reduces to or mimics the prior art approaches.

Experimental Methodology: Combinatorial Dataset Design

Generally, all calculations and analyses to conduct combinatorial chemistry screening library design and follow up are implemented in a modern computational chemistry environment using software designed to handle molecular structures and associated properties and operations. For purposes of this Application, such an environment is specifically referenced. In particular, the computational environment and capabilities of the SYBYL and UNITY software programs developed and marketed by Tripos, Inc. (St. Louis, Mo.) are specifically utilized. Unless otherwise noted, all software references and commands in the following text are references to functionalities contained in the SYBYL and UNITY software programs. Software with similar functionalities to SYBYL and UNITY are available from other sources, both commercial and non-commercial, well known to those in the art. A general purpose programmable digital computer with ample amounts of memory and hard disk storage is required for the implementation of this invention. In performing the methods of this invention, representations of thousands of molecules and molecular structures as well as other data may need to be stored simultaneously in the random access memory of the computer or in rapidly available permanent storage. The inventors use a Silicon Graphics, Inc. Challenge-M computer having a single 150 Mhz R4400 processor with 128 Mb memory and 4 Gb hard disk storage space. SPL (Sylbyl Programming Language) code to implement a preferred method of this invention is set forth in Appendix "A".

Figure 2:
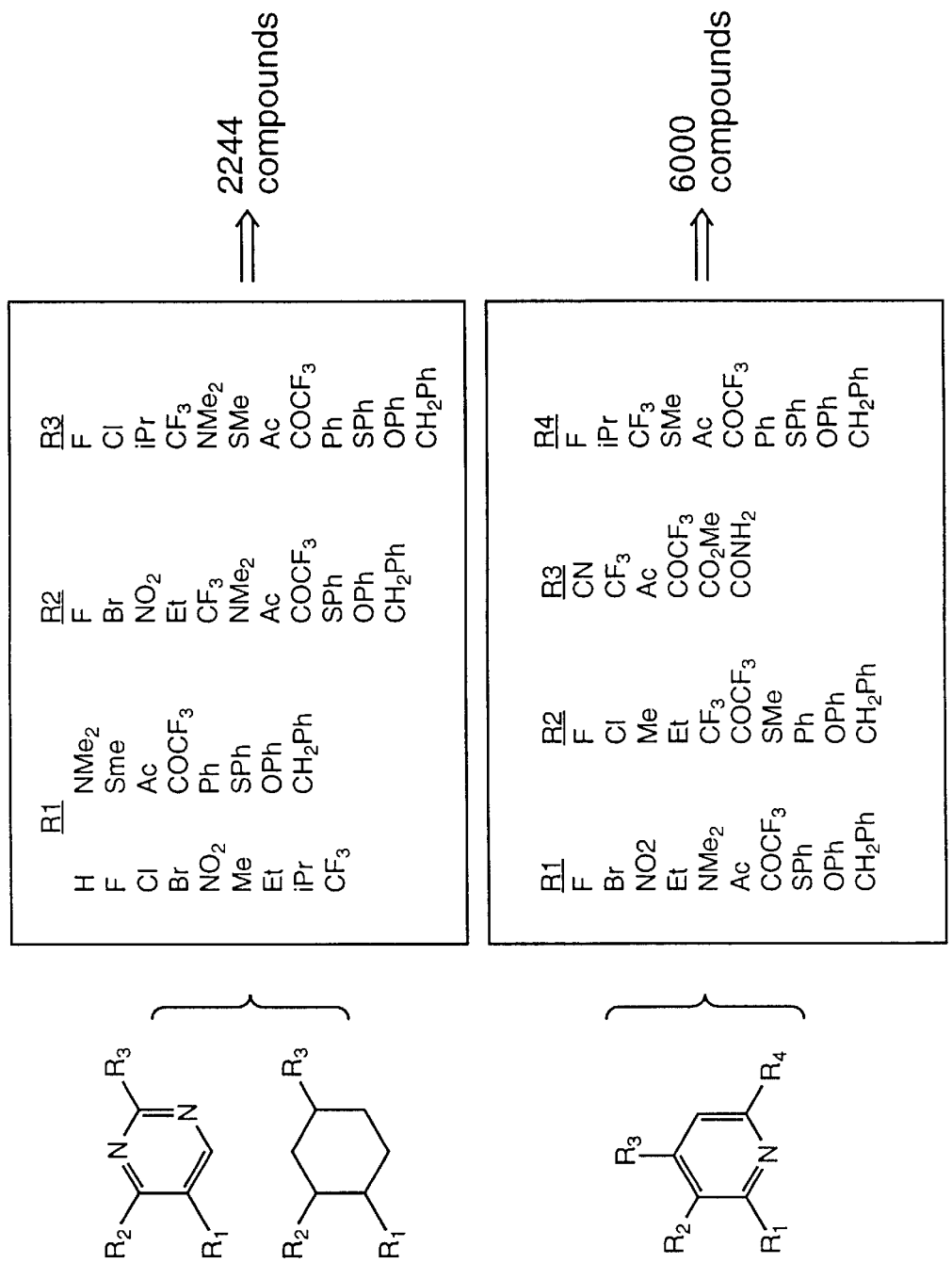
FIG. 2 shows the design of the parent libraries contributing to the combinatorial dataset.

The Legion[13] combinatorial builder module in SYBYL[13] was used to create a homologous set of libraries, each with a pyrimidine, a cyclohexane or a pyridine at the core (FIG. 2) and an analogous pattern of substitution around each ring. The pyrimidine and cyclohexane libraries consisted of 2244 compounds each, whereas the pyridine library was made up of 6000 compounds. A composite library was built from the 6000-compound pyridine dataset, 500 randomly selected cyclohexanes and 100 randomly selected pyrimidines. The final dataset of 1000 compounds—892 pyridines, 92 cyclohexanes and 16 pyrimidines—was created by randomly selecting from among the 6600 compounds in the composite library. The Tanimoto dissimilarity T* (equivalent to the Soergel distance [14,15]) was used to assess the dissimilarity between any two compounds a and b in the dataset:

$$T^* = 1 - \frac{\text{No. Of Bits Occuring} \in \text{Both Molecules}}{\text{No. Of Bits} \in \text{Either Molecule}}$$

The Tanimoto fingerprint simply expresses the degree to which the substructures found in both compounds is a large fraction of the total substructures. Standard UNITY[13] 2D fingerprints were used for evaluating dissimilarities.

Figure 3:
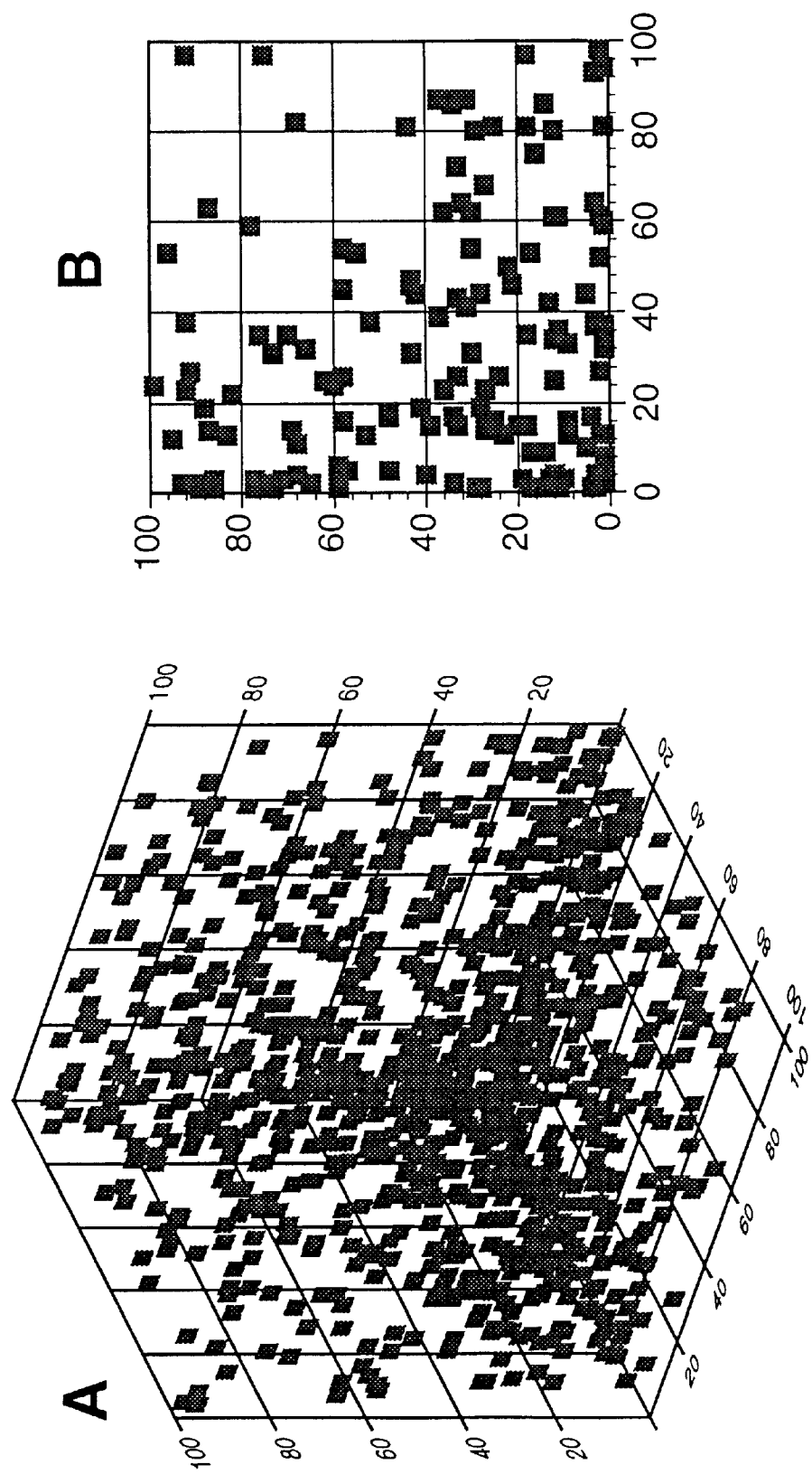
FIG. 3 shows the distribution of scalar descriptors for the combinatorial dataset. (A) Data for all 1000 compounds is displayed in three dimensions. (B) Distribution for 150 compounds in the XY plane.

Three scalar descriptors were generated for the combinatorial dataset by drawing three numbers for each compound from a uniform random population of reals between 0 and 1, then squaring each number and multiplying it by 99. Adding 1 to the integer part of each value produced three descriptors for each compound with values between 0 and 100. These were distributed independently of the 2D structure and, hence, of the corresponding fingerprints. The distribution of values in the resulting scalar three-descriptor space forms a gradient of density running out from the concentration of points near the origin (FIG. 3). Dissimilarity was evaluated in terms of Euclidean distance when using these descriptors to evaluate the performance of OptiSim on multiple scalar descriptors.

$\chi^2$ comparisons: Subsets generated by Optimal Dissimilarity Selection at various subsampling levels K were characterized non-parametrically in terms of the $\chi^2$ statistic:

$$X^2 = \Sigma(O_i - E_i)^2/E_i$$

where $O_i$ denotes the observed count obtained from the $i^{th}$ of c clusters and $E_i$ denotes the count expected from that cluster[16] (the term "cluster" is used here because the comparisons of most immediate interest are between cluster-based selection and OptiSim results; "category" or "class" would be equally appropriate).

The $\chi^2$ statistic with respect to a random sample is a measure of how representative a particular selection set is. In general, the expected count for random sampling is given by:

$$E_i(\text{random}) = b \, M \, n_i/N$$

where b is the number of trials in each block; M is the number selected per trial; $n_i$ is the number of compounds in the $i^{th}$ cluster; and N is the total number of entities being selected from. For random sampling, one expects to select most often from the most populous cluster, and to select proportionately less often from smaller clusters. The larger a selection set's value of $\chi^2$ (random), the more it diverges from being representative of the dataset as a whole.

Note that the OptiSim method of this invention explicitly precludes re-selecting any compound, whereas the random selection distribution is for sampling with replacement. As a result, the selections are not strictly independent of each other and (2) is not exact. This is not a problem if the number of selections per trial does not greatly exceed the number of clusters. It is then necessary, however, to block trials if one is to keep the expected number of selections for each cluster large enough to avoid having to make a continuity correction to the $\chi^2$ statistic calculated in (1).[16]

If selection is perfectly uniform across clusters, each cluster will be equally likely to be sampled. How uniformly a selection is distributed across c clusters, then, is a measure of how similar a result is to cluster-based selection. The $\chi^2$ (uniform) statistic is therefore calculated from:

$$E_i(\text{uniform}) = b \, M/c$$

Again, perfect concordance gives a $\chi^2$ of 0. The smaller $\chi^2$ (uniform) is, the better the result mimics cluster-based selection.

Scaling: As noted above, a perfectly random selection will have a $\chi^2$ (random) of 0, and a perfectly uniform selection will have a $\chi^2$ (uniform) of 0. Both results, however, are quite unlikely when selections are made independently. For either statistic, the mean $\chi^2$ expected by chance is equal to the degrees of freedom (df=c−1). Scaling by this population mean makes it easier to compare experiments which involve different numbers of clusters (i.e., categories of classification), since it makes the expected result equal to 1 no matter how many clusters are involved.

Experimental Results—Power of Optisim Methodology

Scalar descriptors: A hierarchical clustering was done in Selector[13] using complete linkage on the three scalar descriptors generated for the 1000 compounds in the combinatorial dataset, which resolved the dataset into ten clusters. Two clusters split one corner of the cubical descriptor space; the rest cover the remaining corners and the center. The ten clusters obtained were made up of 283, 167, 134, 130, 90, 78, 45, 29, 24 and 20 compounds, respectively. Not surprisingly, the largest cluster is near the origin and the smallest is at the opposite vertex of the cubical boundaries of the descriptor space.

Optimal Dissimilarity Selection was then applied to the dataset 20 times at each of seven different subsampling rates K, selecting ten compounds ($M_{max}$=10) each time; R was set to 10. The same random number was used to "seed" the method for one trial at each subsampling rate, so any biases due to the initial selection were spread equally across all values of K. The number of selections from each cluster was summed across a block of ten such trials, so that each block included 100 selections for each subsample size. The $\chi^2$ statistics obtained were then averaged across two such blocks. The total number of scalar selections was therefore:

(10/trial)×(10 trials/block)×(2 blocks)×(7 subsampling rates)=1400 in 140 trials, with a total of 200 selections made for each subsampling rate.

The distributions of these selections across clusters were then compared to the totals expected for random sampling and to the totals expected for uniform selection from the ten clusters. Table 1 shows the $\chi^2$ values obtained as averages across two blocks for each value of K.

TABLE 1

Divergence of subsets selected from the combinatorial dataset from random and uniform distributions across clusters. Values cited are in terms of scaled chi squared ($x^2$/degrees of freedom).

| $K^a$ | scalars (df = 9) | | fingerprints (df = 20) | |
|---|---|---|---|---|
| | random[b] | uniform | random | uniform |
| 1 | 1.23 ± 0.43[c] | 7.21 ± 0.14 | 0.89 | 15.05 |
| 5 | 2.06 ± 0.50 | 3.56 ± 0.51 | 4.04 | 7.36 |
| 10 | 2.58 ± 0.11 | 2.44 ± 0.11 | 11.15 | 5.56 |
| 15 | 5.04 ± 0.66 | 1.98 ± 0.24 | 13.75 | 3.94 |
| 25 | 5.88 ± 1.16 | 1.93 ± 0.38 | 20.32 | 3.38 |
| 35 | 7.61 ± 2.89 | 2.02 ± 0.07 | 26.74 | 2.08 |
| 1000[d] | 7.59 ± 0.72 | 0.67 ± 0.15 | 49.84 | 2.05 |

[a]Subsampling rate at each iteration.
[b]Reference distribution.
[c]Mean ± SEM for two blocks.
[d]All unselected compounds considered at each iteration.

The $\chi^2$ (random) for minimal dissimilarity selection (K=1) is not significantly different from that expected by chance (1.23 vs 1.0), but it rises steadily with increasing K as the selected subsets grow more diverse and less representative. The $\chi^2$ (uniform) profile, on the other hand, falls quickly with increasing K to a plateau value of about 2 for K=15–35. The maximal dissimilarity extreme (K=1000) produces a significantly more uniform distribution (0.67 vs ~2.0), which reflects the fact that a cluster is, in this case, located at each of the first nine linear D-optimal points of the descriptor space—the corners plus the center.

Note: maximum dissimilarity selection (K=1000) performs unusually well here with respect to hierarchical clustering in part because the dimensionality (3) is much smaller than $M_{max}$ (10), and in part because the peak population density near the origin coincides with one extreme of the descriptor space.

Figure 4:
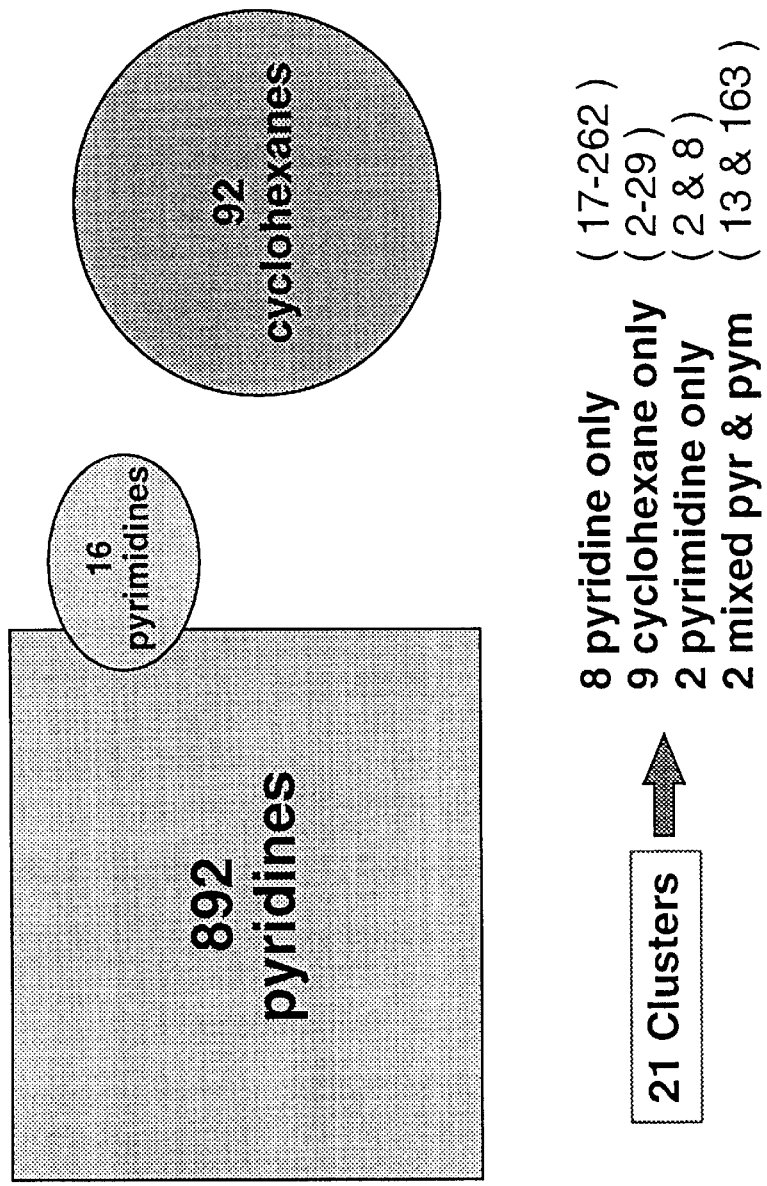
FIG. 4 shows the relationships among compound classes in the combinatorial dataset as shown by hierarchical clustering on UNITY 2D fingerprints.[13]

Combinatorial fingerprints: Hierarchical clustering of the combinatorial dataset using 2D fingerprints gave 21 clusters as a "natural" level (see discussion above of hierarchical clustering). These included 19 "pure" clusters made up of 262, 152, 75, 64, 64, 45, 43 or 17 pyridines; 29, 21, 11, 10, 6, 5, 5, 3 or 2 cyclohexanes; and 8 or 2 pyrimidines. Two mixed clusters contained both pyridines and pyrimidines— 161 and 2, or 9 and 4, respectively. The relationships between the sublibraries shown by this clustering pattern are illustrated schematically in FIG. 4. Note that the areas of each set shown in FIG. 4 indicate the number of compounds of that class which are in the dataset, not the degree of diversity within each class. Because they are drawn from homologous combinatorial libraries, the degree of structural variety found within each class is similar. This is reflected in the similar numbers of pyrimidine and cyclohexane clusters; that fewer pyrimidine clusters were identified simply reflects their scarcity.

Twenty-one compounds were selected in each trial ($M_{max}$=21), and distributions across clusters were summed across 10 trials for each block at each of seven values of K; R was set to 0.15.[9,10] Again, there was one trial at each subsampling rate for each random number seed used; the seeds used were different from those used for analyzing the associated scalar descriptors. In this case, blocks were not replicated. Hence the total number of trials was:

(21/trial)×(10 trials/block)×(7 subsampling rates)=1470 in 70 trials, with a total of 210 selections made at each of 7 values of K.

The values of scaled $\chi^2$ found with respect to random and uniform distributions are shown in Table 1. Again, the OptiSim selections move away from being purely representative and begin to resemble cluster-based selection even at low values of K. Note that under this high-dimensional, non-Euclidean metric the limiting scaled $\chi^2$ (uniform) is 2.0.

Again, maximum dissimilarity (K=1000) returned the most uniformly distributed selection set. Note, however, that the number of superclusters (3—one for each of the constituent combinatorial core structures) is small compared to $M_{max}$ (here, 23). The distribution of compounds chosen using maximum dissimilarity selection can be uncharacteristically uniform in such a situation.

Mannhold-Rekker dataset: The combinatorial dataset described above is very structured and artificial. It was created so deliberately in an effort to keep evaluation of the selection method—OptiSim—separate from the considerations of the appropriateness of the particular metric being used. Nonetheless, it is important to know how well the methodology performs with more realistic datasets. Mannhold et al.[17] compiled a database of 68 structurally diverse compounds from six pharmacological classes for evaluating different ways of predicting a compound's octanol/water partition coefficient P from its structure. The dataset includes 15 class I antiarrhythmics, 13 phenothiazines, 12 class III antiarrhythmics, 11 β-blockers, 9 benzamides and 8 potassium channel openers. OptiSim was used to select six compounds from the dataset in nine trials with K set to 1, 3, 5, 7, 10 or 68. Again, standard UNITY 2D fingerprints were used to evaluate the dissimilarity between molecules.

Figure 5:
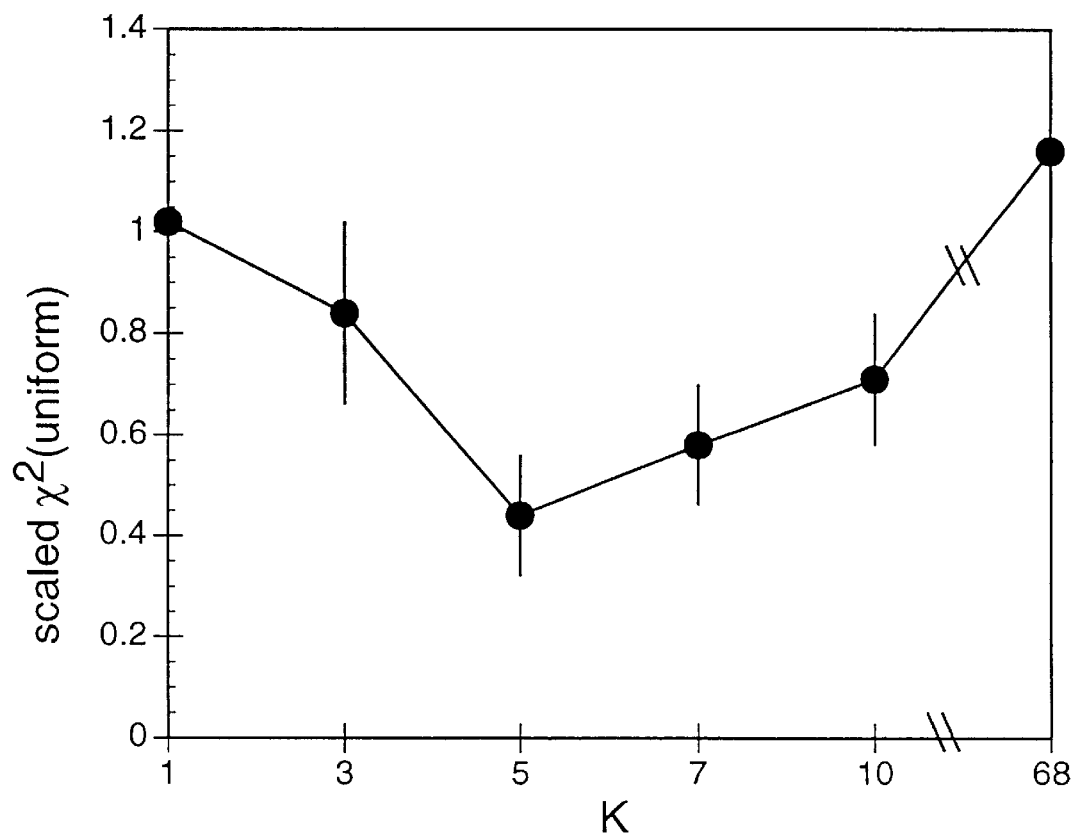
FIG. 5 shows the divergence of OptiSim selections from uniform sampling across pharmacological classes for the Mannhold-Rekker dataset[17] as a function of subsample size K. The $\chi^2$ statistic is scaled by division by its 5 degrees of freedom.

In this case, the uniform reference distribution was based on pharmacological classes. Because there is relatively little variation in population between classes in this dataset, however, the analysis applied above to the combinatorial dataset is not very informative, particularly vis à vis random sampling. Instead, $\chi^2$ (uniform) was calculated for each trial, and the results averaged across the nine trials for each subsampling rate K. The results obtained are shown in FIG. 5; selection of one example from each pharmacological class was best reproduced at K=5–7.

Note that here, where the underlying complexity of the dataset (6) is comparable to $M_{max}$, intermediate values of K outperform maximum dissimilarity. In fact, OptiSim actually performs somewhat better with respect to the pharmacological classes in this dataset than does cluster-based selection based on 2D fingerprints and complete-linkage (data not shown), in part because the variation in structures within classes is uneven.

Parametric measures of diversity and of representativeness: The $\chi^2$ statistic is a good measure of similarity for validation work, but it requires a reference distribution and so is of limited usefulness when no hierarchical classification is available for comparison. If Optimal Dissimilarity Selection is to be used as a surrogate for hierarchical clustering, more readily accessible measures will be needed to know when the optimal balance between representativeness and diversity has been obtained for a given subsample size in any particular application.

It is convenient to use averages when characterizing large datasets, because the law of large numbers guarantees that a good estimate of the average can usually be obtained from a random sample of the entire dataset.[18] If S is the set of M compounds selected and U is the set of n compounds chosen randomly from among those compounds which were not selected, then the average dissimilarity δ between each compound in S and the other compounds in S is a measure of diversity, whereas the average dissimilarity ρ between compounds in S and those in U is a measure of representativeness. The minimum pairwise dissimilarity criterion[2,3] for evaluating the dissimilarity between each compound and the reference set is being used, so:

$$\delta = (1/M) \sum_{i=1}^{n} \min(T^*(s_i, s_j) : 1 \leq j \leq M, i \neq j)$$

$$\rho = (1/n) \sum_{i=1}^{n} \min(T^*(u_i, s_j) : 1 \leq j \leq M)$$

Figure 6A:
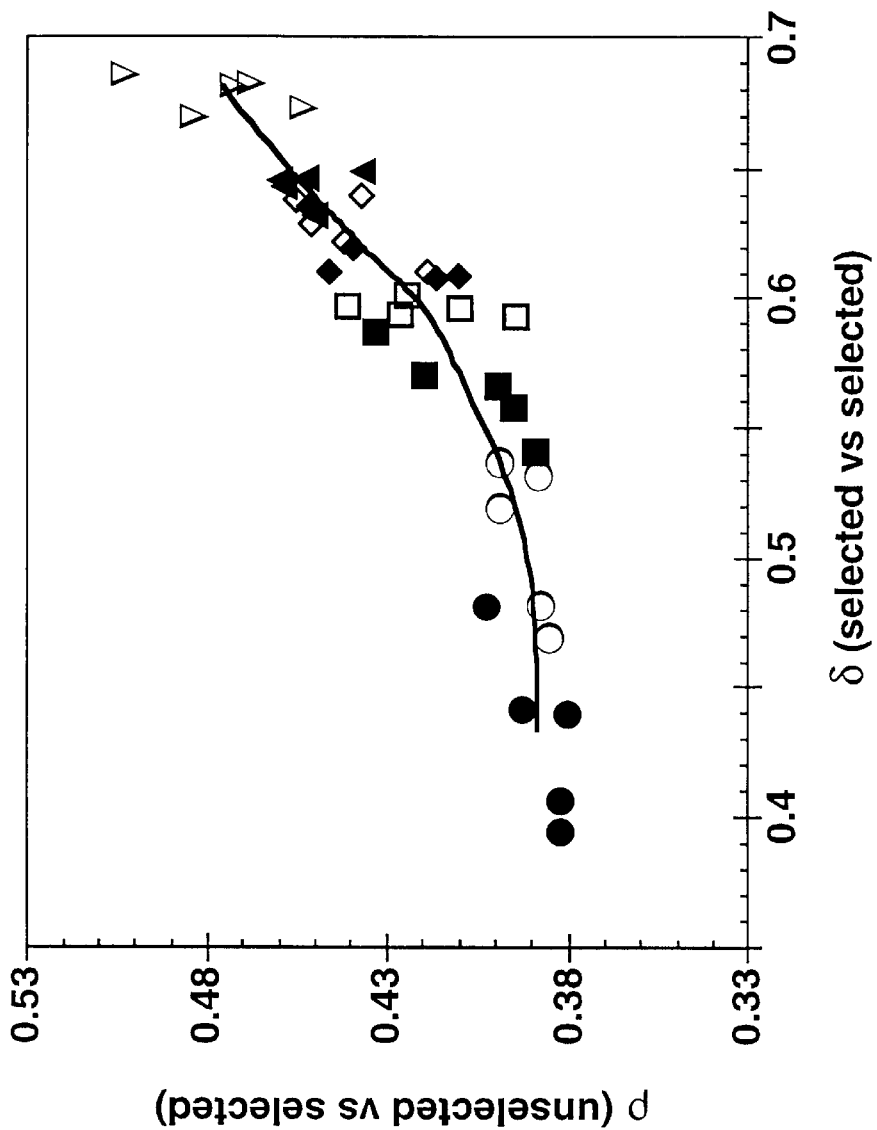
FIG. 6A shows the relationship between the average dissimilarity ρ between unselected compounds and sets of 21 compounds selected by OptiSim as a function of the average dissimilarity δ among selected compounds. One of two sets of 100 compounds randomly selected from the combinatorial dataset was used to calculate ρ for each trial. The data shown is for UNITY 2D fingerprints from the combinatorial dataset. (●) K=1; (○) K=2; (■) K=5; (□) K=10; (♦) K=15; (◊) K=25; (▲) K=35; (▽) K=1000; (–) spline curve drawn through the mean values of ρ and δ for each value of K.
Figure 6B:
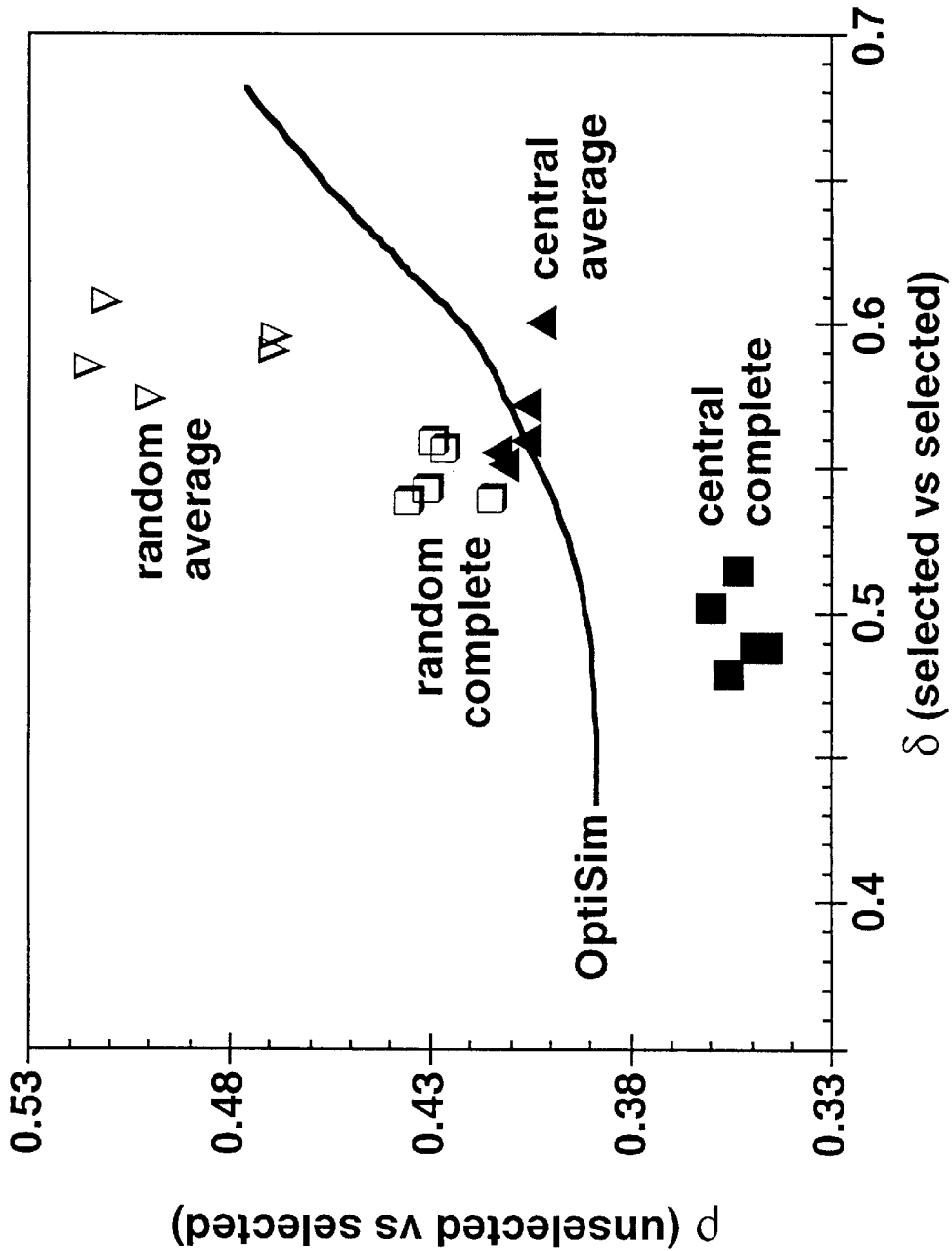
FIG. 6B shows the relationship between the average dissimilarity ρ between unselected compounds and sets of 21 compounds selected by hierarchical clustering as a function of the average dissimilarity δ among selected compounds. (■, □) selections made from hierarchical complete linkage clusters[8]; (▲, ▽) selections made from hierarchical group average clusters[8]; (□, ▽) one compound was randomly selected from each cluster; (■, ▲) one compound was randomly selected from among the three most central compounds in each cluster; (–) spline curve corresponding to that shown for Optisim selections in FIG. 6A.

FIG. 6A shows a plot of ρ as a function of δ for fingerprints from the combinatorial dataset; for clarity, only five trials at each of seven levels of subsample size K are shown. Data are also shown in FIG. 6B for both unbiased random selection of one compound from each of the hierarchical clusters described above (labelled "random" in FIG. 6B), and for random samplings from among the three most central compounds in each cluster[19] (labelled "central" in FIG. 6B; this is a Tanimoto space, so "central" compounds are not necessarily representative). Results from both complete linkage and group average hierarchical clustering are shown.

The scatter in ρ and δ among selection sets obtained at the same value of K reflects the random sampling component of the method. The variance in δ falls sharply as K increases, with a standard deviation (SD) of 0.043, 0.012 and 0.010 at K=1, 5 and 35, respectively. For any particular dataset and a given $M_{max}$, there is a characteristic limiting value for δ. In this case, $\delta_{max}$ is slightly less than 0.7.

The variance in ρ, on the other hand, is primarily determined by the randomly chosen unselected compounds (U) to which the selection sets are compared, and so decreases only slightly with increasing K. Note that for OptiSim selection sets, ρ and δ will both be smallest (on average) when K=1. Moreover, the expected values for ρ and δ will be equal if and only if: S and U are the same size; R=0; and K=1.

As expected, an increase in diversity (δ) comes at the cost of a decrease in representativeness (increase in ρ). Also as expected, minimum dissimilarity selection (K=1) returns a selection set more representative (lower ρ) but less diverse (lower δ) than does cluster-based selection. Maximum dissimilarity selection (K=1000) increases diversity at some cost in representativeness, particularly with respect to selection from among the central compounds in each cluster (C).

The results for K=5, 10 and 15 show something quite unexpected, however. At these subsampling rates, OptiSim returns selection sets which are both more representative (lower ρ) and more diverse (higher δ) than are the cluster-based selections. This difference in the quality of the selections made accounts for the failure of $\chi^2$ (uniform) to fall much below 2 for this dataset when hierarchical clustering is taken as the reference distribution.

Recall that the hierarchical clustering used as a reference is based on complete linkage.[8] Ward's method is an alternative approach which uses a probabilistic, least-squares rationale to maximize distances between clusters while minimizing distances within clusters under Euclidean metrics.[20] Evidently, Optisim's sampling approach imparts similar properties to its selection sets. This is potentially a quite useful generalization, since Ward's method is not applicable to metric spaces in which centroids of clusters are not well-defined—in particular, it is not directly applicable to Tanimoto coefficients based on 2D fingerprints or other bit set descriptors.

It has been determined by applying the method of this invention through extensive testing, that there is little or no advantage in selecting a value of K greater than the square root of N. For instance, it can be seen in FIG. 5 that the scaled $\chi^2$ has a minimum (~5) for a K<$\sqrt{68}$. In addition, in FIG. 6A, it can be seen that most of the diversity ($\delta$) obtainable (as indicated by K=N, 1000) is achieved with a K=35, approximately the square root of 1000. Also, by the time K is as large as $\sqrt{N}$, it can be seen that ($\rho$) representativeness is being lost ($\rho$ higher value) indicating, perhaps, that in this example K=$\sqrt{N}$ may already be too high. Thus, the fundamental number of steps for the method of this invention is proportional to or less than $\sqrt{N}$.

The $\rho$ vs $\delta$ plot such as in FIG. 6A is one way to compare different selection sets. Another way is to apply hierarchical clustering to the selection sets themselves. It is then possible to compare the dendrograms produced by such analyses to qualitatively assess the similarities and differences between the selection sets. This is illustrated for single linkage, group average, and complete linkage hierarchical clustering methods in FIG. 8. The 1000 compound mixed dataset was partitioned into 30 clusters for each method, and a representative compound was drawn from among the three most central compounds in each cluster. Those representations were then themselves clustered to give the dendrograms shown in FIG. 8. For the sake of consistency, this secondary clustering was done using complete linkage in each case. The class of compounds making up each cluster is indicated at the base of the dendrogram, where each vertical line corresponds to the selected representative from one cluster.

Based on the dendrograms and on the relative number of pyrimidine and pyridine structures selected, it is clear that the single linkage is the most biased towards unusual structures (pyrimidines) and so gives the most diverse, but least representative selection. Indeed, many of the single linkage clusters are pyrimidine singletons, and the 90% of the dataset comprised of pyridines are lumped together into just seven large clusters. Complete linkage clustering, on the other hand, is skewed towards a better representation of the more common class of compounds (pyridines) and is correspondingly less diverse. Group average clustering provides an intermediate balance in discrimination among and between classes.

Figure 8:
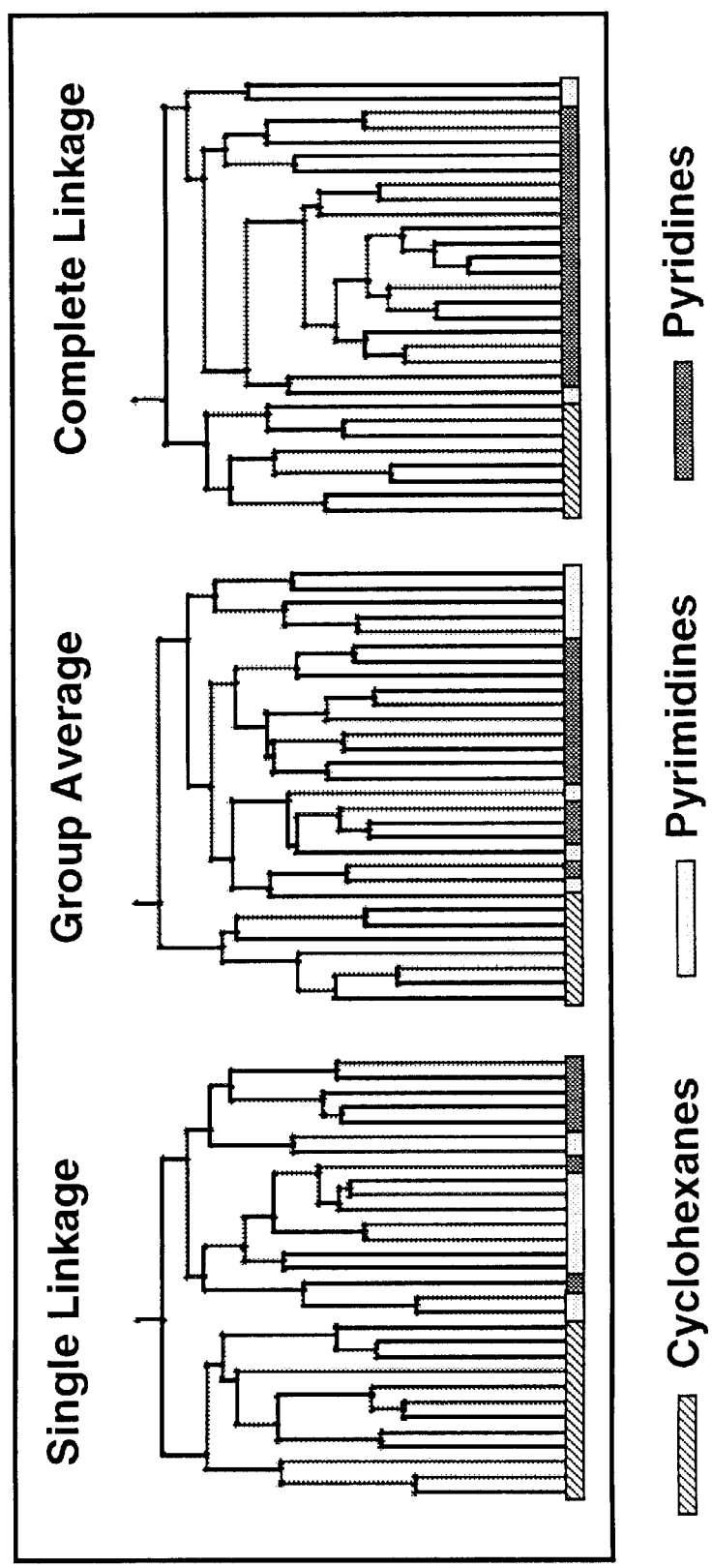
FIG. 8 shows the dendrograms produced by using single linkage, group average, and complete linkage hierarchical clustering to select 30 compounds.
Figure 9:
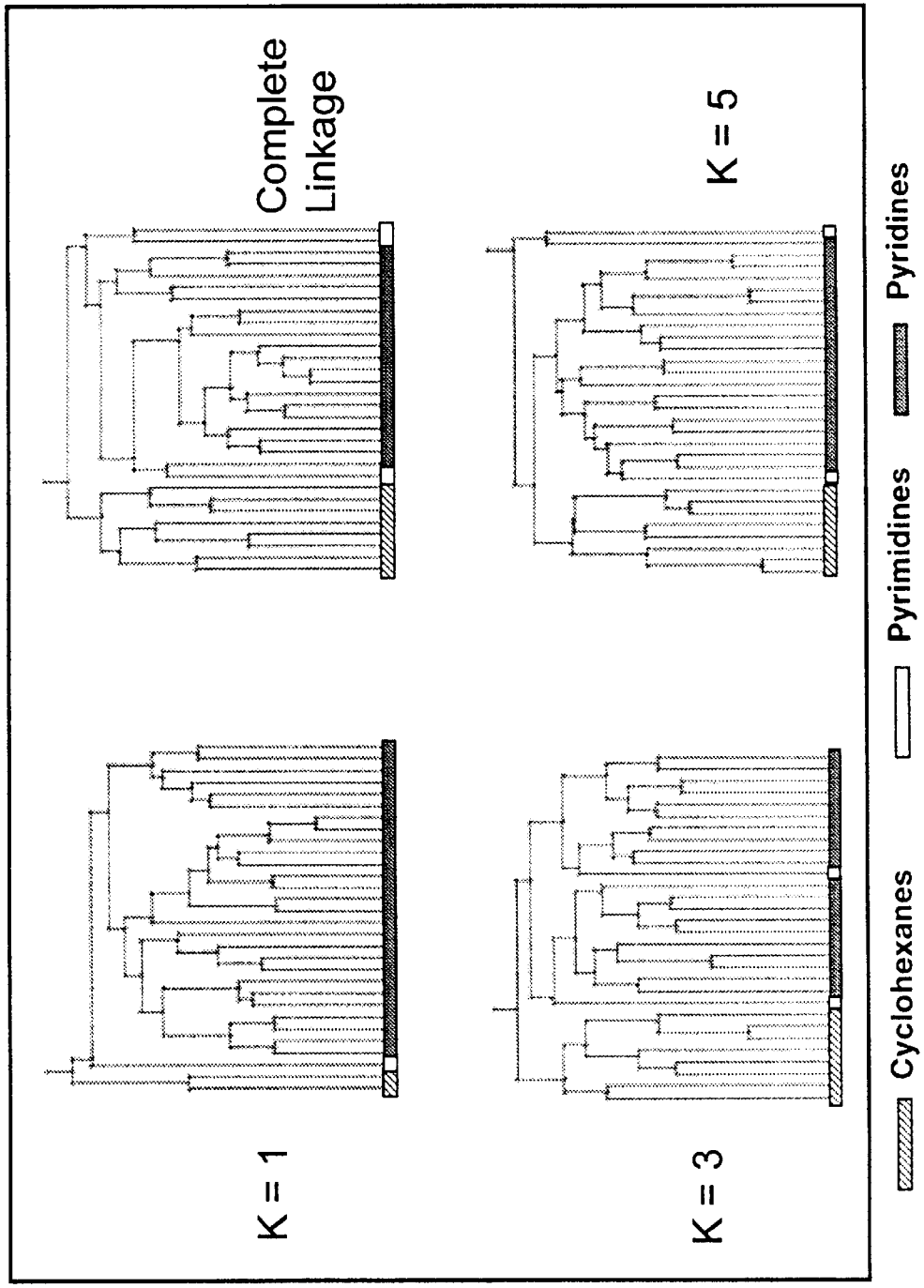
FIG. 9 shows dendrograms analogous to those of FIG. 8 for Optisim selections made with K=1, 3, and 5. The complete linkage dendrogram from FIG. 8 is repeated for comparison.

FIG. 9 shows analogous dendrograms to those of FIG. 8 but obtained using the Optisim method with K=1 (minimum dissimilarity), K=3, and K=5. At the smallest subsample size (K=1), the selection is almost purely representative, with only one pyrimidine and two cyclohexanes being selected. This reflects their numerical contributions to the dataset (2% and 9% respectively) reasonably well. As expected from the $\rho$ vs $\delta$ plot of FIGS. 6A and 6B, the complete linkage selection is mimicked reasonably well by the K=5 selection set. This comparison illustrates another aspect of the similarity between the Optisim methodology and cluster based selection.

Variations and Extensions of the Basic Optisim Methodology

The heart of the Optimal Dissimilarity Selection approach lies in taking a series of random subsamples from a dataset, and selecting the best candidate from each subsample, where "best" is defined by some preference criterion which is a function of those compounds (or, more generally, elements) which have been selected in previous steps. Several useful variations on the method disclosed in this document will be immediately apparent to those skilled in the art. The following variations as well as others enabled by the disclosure in this document are considered within the scope of this disclosure.

Other evaluation criteria: OptiSim has been defined here solely in terms of maximum minimum pairwise dissimilarity to those compounds already selected as the criterion by which the "best" compound is to be selected from each subsample. The highest average dissimilarity[3] could just as well be used, and the cosine coefficient[11] could be substituted for the Tanimoto coefficient. In fact, the method is generalizable to any set of selection criteria or decision rules—best priced or most synthetically accessible compound, for example, or lowest price in the highest quartile in dissimilarity. The redundancy test against R can also be defined more broadly.

Similarly, selection for each subsample need not be random, but can be systematically biased towards compounds in combinatorial libraries which share reagent "parents" with compounds which have already been selected. An analogous scheme is currently implemented in DiverseSolutions[6] for descriptors of low dimensionality in a cell-based selection system.

Sampling with replacement: As set out in FIG. 1, each OptiSim subsample is drawn from the candidate pool for consideration, then is set aside until all candidates have been examined once—i.e., the dataset is sampled without replacement. If samples are drawn with replacement of those compounds which do not get selected, no recycling bin is required. A given setting of K will then return a more representative but less diverse subset because sampling of more sparsely populated (outlier) regions will be avoided. The tradeoff will be that a particular level of diversity among the compounds selected will only be approached at higher values of K, which can become computationally expensive.

Replacement of redundant compounds in the subsample: The implementation described in FIG. 1 tests each compound in the subsample for redundancy, and replaces any redundant compounds in the subsample before selecting the best one in that subsample. An alternative approach is to apply the redundancy test only to that best compound; if it is redundant—that is, if it is too similar to those which have already been selected—no selection from that subset is made. This approach can be made faster "up front" than the version of OptiSim set out in FIG. 1 for some descriptors and similarity measures, but will be correspondingly slower at later selection steps. In addition, the balance between representativeness and diversity will be shifted towards making more representative selections, just as subsampling with replacement will.

Dataset clustering: As demonstrated here, OptiSim selection sets behave very much like selection sets based on hierarchical clustering. OptiSim selections can be used as centers (i.e., as leaders[1]) for efficiently clustering large datasets on the basis of a secondary similarity radius, R', or by assignment of each compound to the most similar center. Moreover, selected compounds can themselves be submitted to hierarchical clustering. Under this scenario, the OptiSim selections will be true centers of their R' neighborhoods[10] for any metric, so their hierarchy will perforce accurately reflect hierarchical relationships across the entire dataset.

Figure 10:
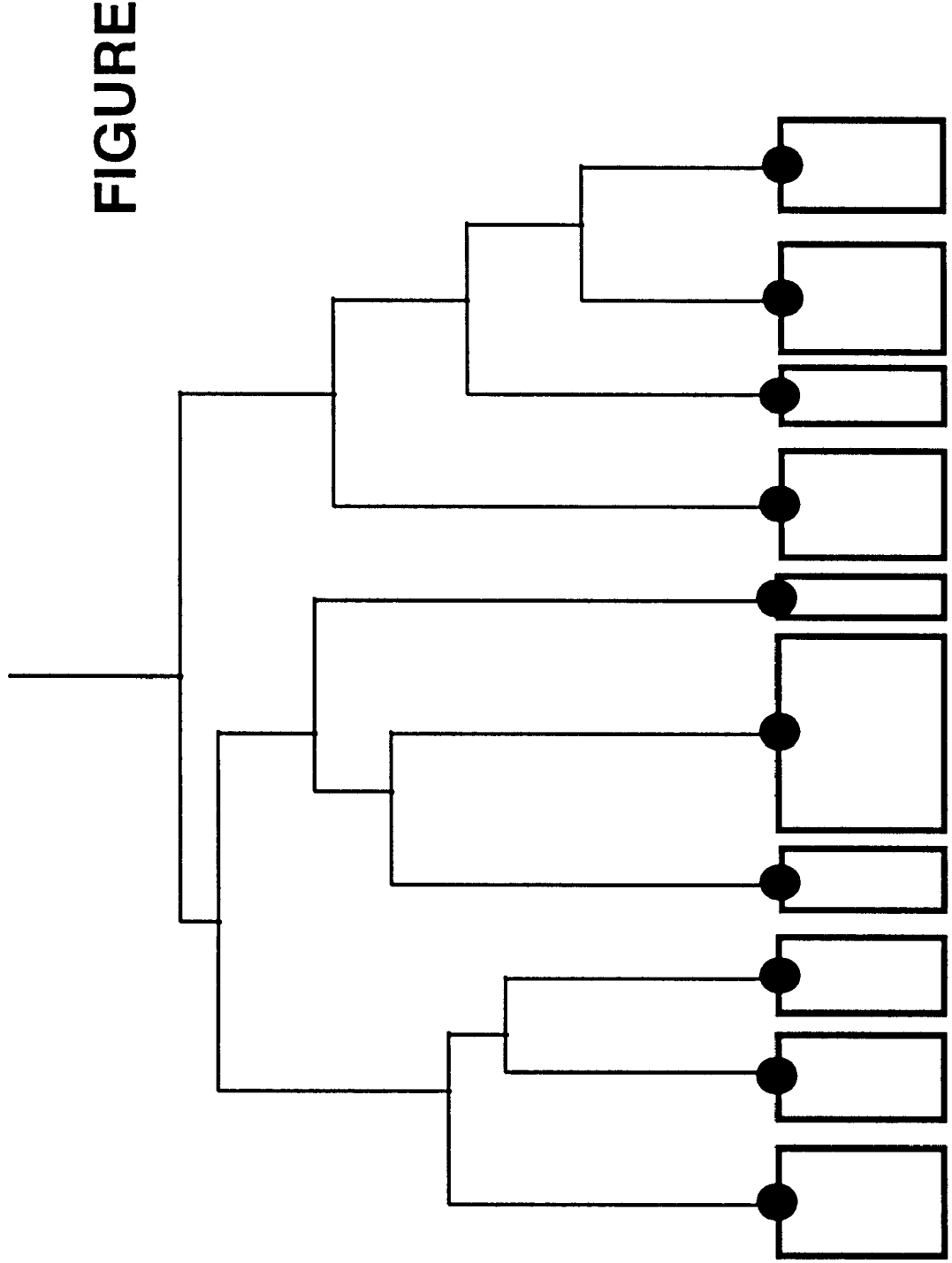
FIG. 10 shows a schematic dendrogram for an Optisim clustering from a selection set of 10 compounds.
Figure 11:
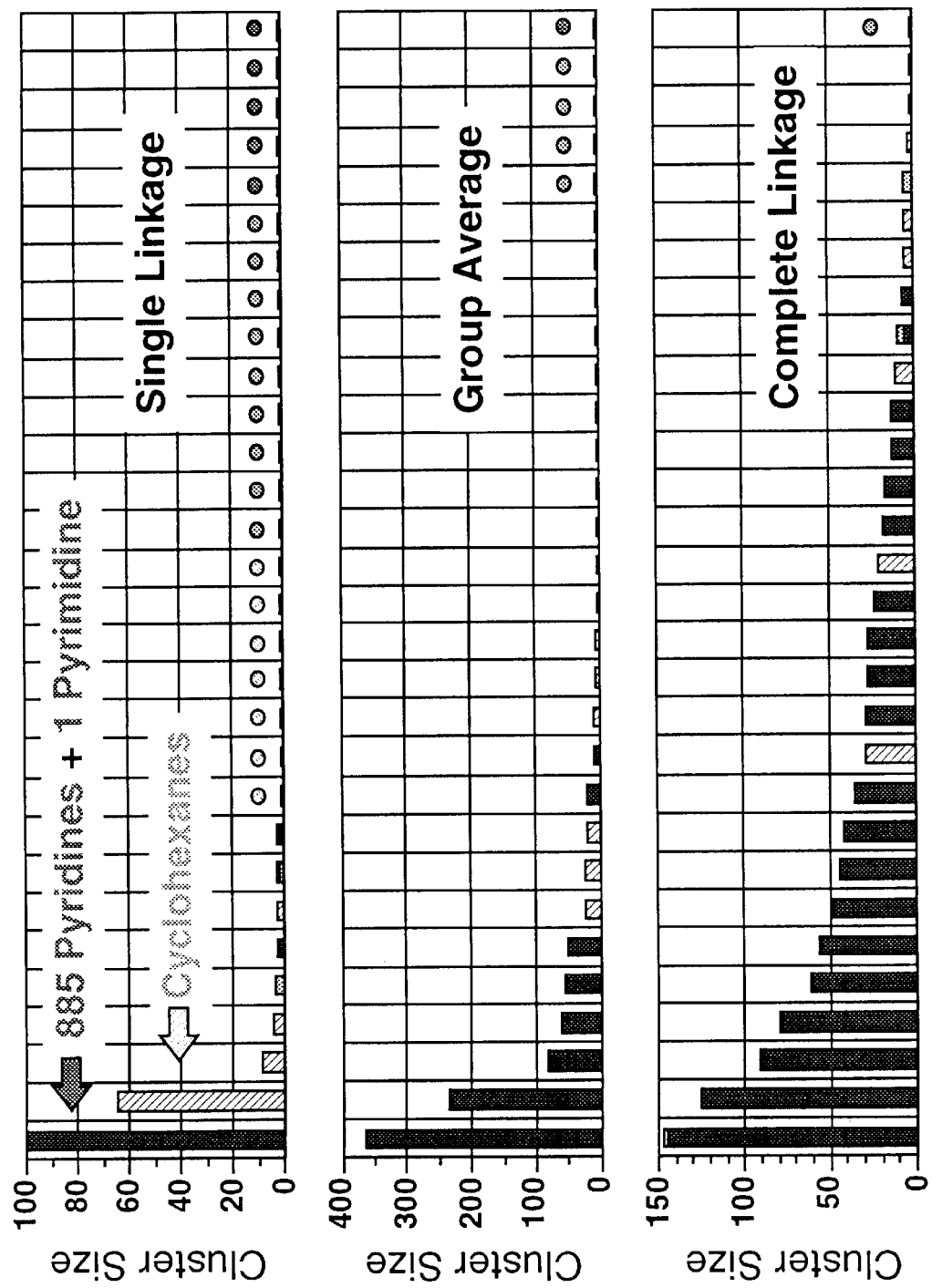
FIG. 11 is a plot of the distribution of cluster sizes obtained from the test data set for single, group, and complete linkage. The bar codings are the same as shown in FIG. 8.

This is illustrated schematically in FIG. 10 for an OptiSim selection set of 10 compounds, with each compound being assigned to the cluster corresponding to the most similar member of the selection set. Note that the process scales intrinsically with (N−M)×M rather than scaling with $N^3$, as hierarchical clustering does $N^2$ where RNN[8] can be used). Such OptiSim clustering makes it possible to compare OptiSim with other clustering methods with respect to cluster size distributions. FIG. 11 shows characteristic cluster size distributions for single linkage, group average and complete linkage methods. Note that here, "size" refers simply to membership count, not to how much of fingerprint space each cluster covers. Pyridine memberships are shown as dark bars, whereas cyclohexanes are indicated by hashed bars and pyrimidines are indicated by stippled bars. Circles indicate the location and identity of singleton clusters.

For single linkage (top), most of the pyridines (89% of the entire dataset) constitute a single large cluster, and only one other cluster of any size is found. The pyrimidines, many of the cyclohexanes and a few pyridines are spread among singletons and doubletons. The clusters obtained using group average clustering show a more useful level of resolution among the pyridines, but still discriminates too effectively among the pyrimidines. Among the methods illustrated in FIG. 11, the most intuitively appropriate balance between representativeness (in this case, discriminating among pyridines) and diversity (discriminating among pyrimidines) seems to be struck by complete linkage clustering (bottom).

Figure 12:
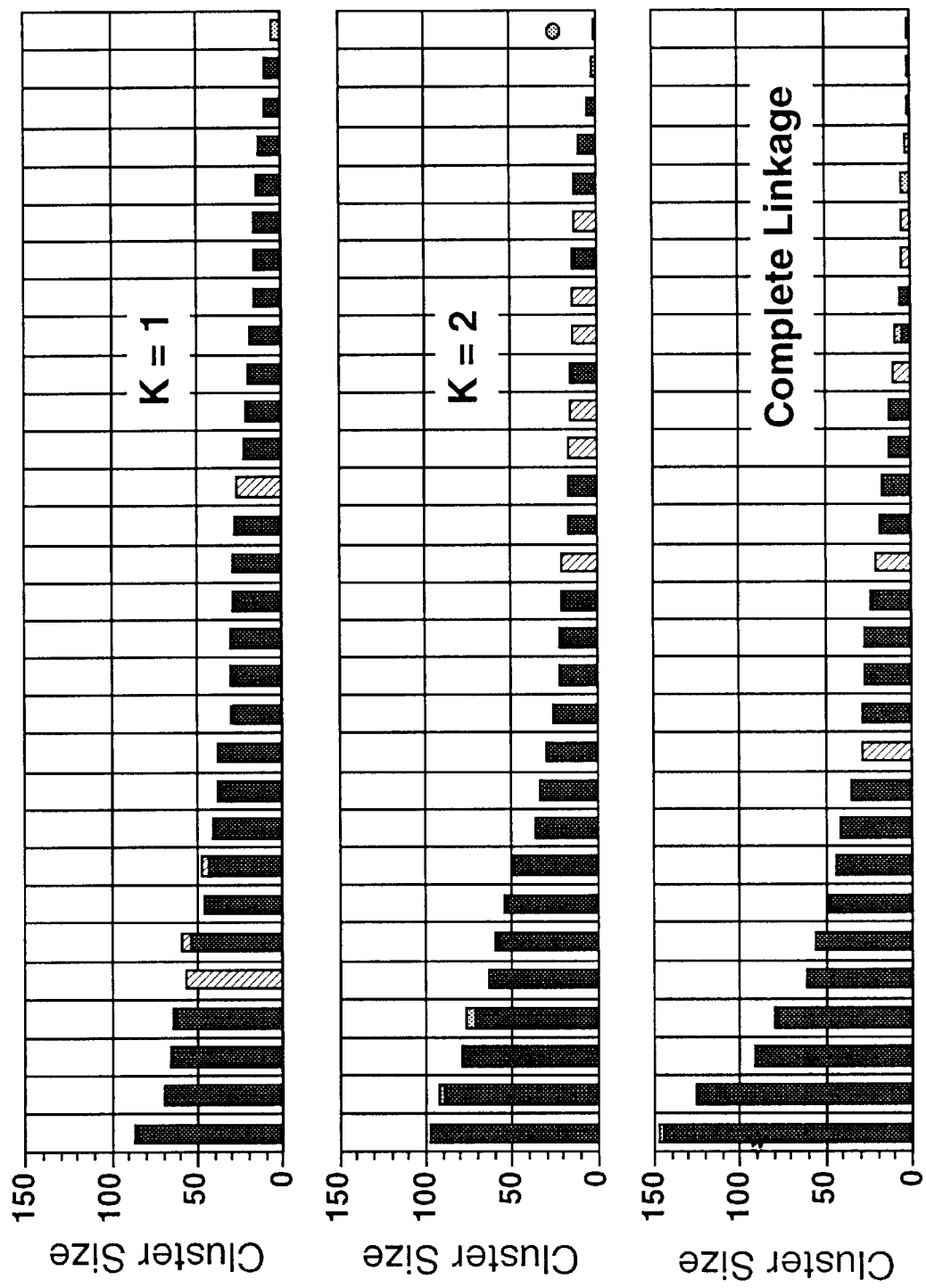
FIGS. 12 and 13 show the comparison of the cluster size distributions obtained from Optisim clusterings based on K=1, 2, 3, and 5 to the complete linkage clustering. The bar codings are the same as shown in FIG. 8.
Figure 13:
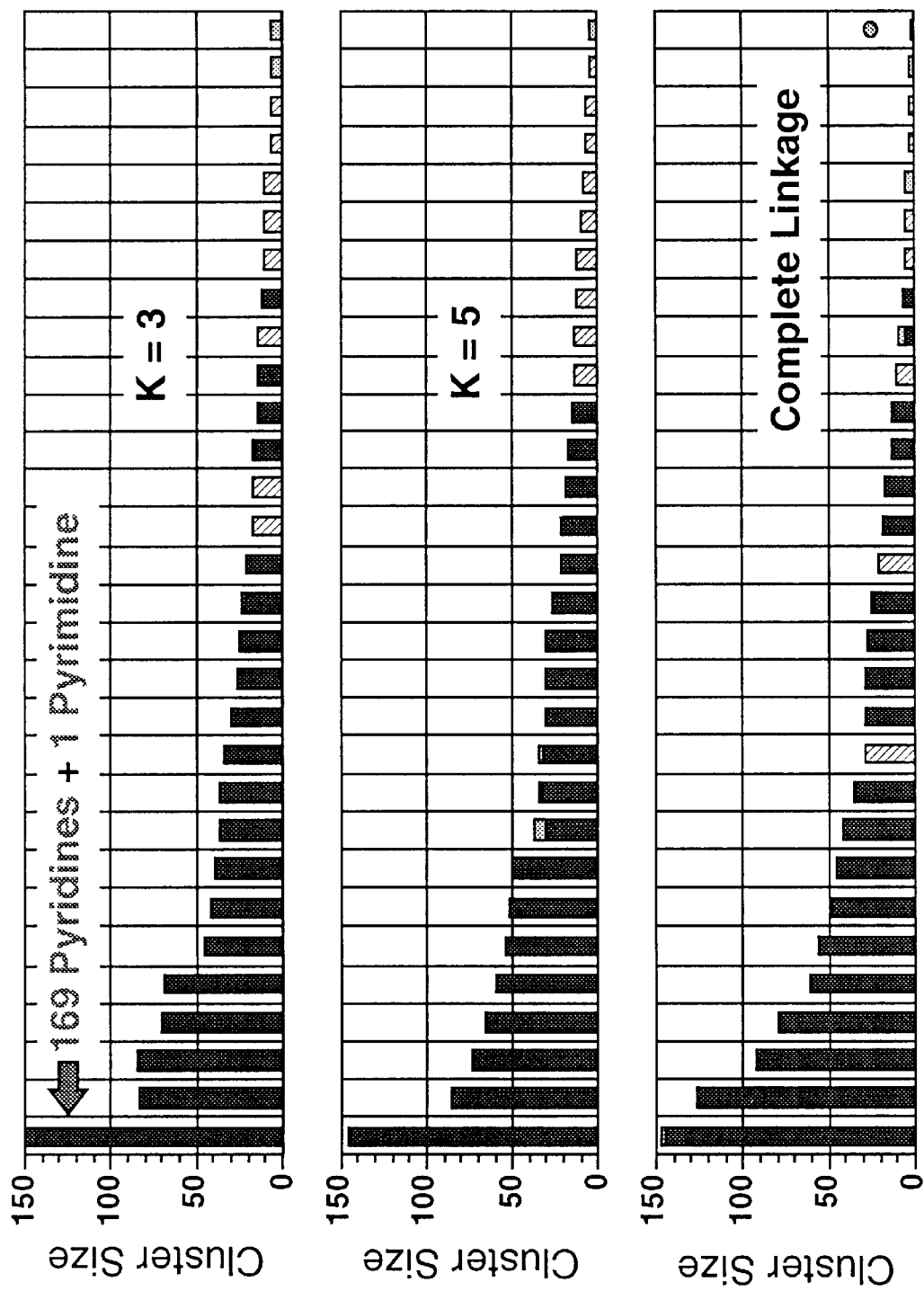

FIGS. 12 and 13 compare the cluster size distributions obtained for OptiSim clusterings based on K=1 and 2 or 3 and 5, respectively. At the smaller subsample size, the clustering is representative in that the pyridines are well distributed across clusters; the uncommon compounds—here, cyclohexanes and pyrimidines—fall into just one or two clusters each. Indeed, in some cases cyclohexanes get lumped in with pyridines. As the subsample size grows, discrimination among the more distinctive compound classes increases, until at K=5 (middle) the distribution is quite similar to that seen for complete linkage clustering (bottom).

There is one respect in which the OptiSim clustering for K=5 differs appreciably from that for complete linkage. Note that the cyclohexane clusters are considerably more even in size in the latter case. This reflects the fact that the OptiSim clusters can and will adjust their diameters (maximum pairwise dissimilarity within the cluster) somewhat to compensate for "local" variations in scale and/or spatial distribution. This flexibility is an advantage over hierarchical methods in general and complete linkage in particular. It arises because the OptiSim selection method is inherently progressive: the first selection by definition represents the whole dataset, and subsequent selections fill in details of areas not yet adequately represented. Indeed, such progressivity is one of the desirable hallmarks of divisive clustering methods[1,9], which are not themselves generally well suited for application to large datasets.

Examples of Broad Applicability of Optisim Methodology

Clinical Trial Design

At present, populations for clinical trials are generally chosen to be as homogeneous as possible. This is done to maximize the sensitivity of the tests to treatment effects. Due to the recognition that subpopulations may exist, there is growing pressure to move away from this paradigm, however, and run clinical trials in more heterogeneous populations. There are several scenarios under which this becomes beneficial:

1) A significant subpopulation exists which reacts badly to the treatment being studied. Heritable allergies and drug interactions fall into this category.
2) The intended benefit is not seen in the general population, but a significant subpopulation exists for which the intended benefit is realized and is of substantial value.
3) There is an unanticipated benefit to the treatment, but one which is only realized in a subpopulation. Hair growth stimulators and impotence relief treatments fall into this category.
4) There is significant systematic variation in response to the treatment, either due to genetics (P450 or other metabolism) or because of interactions with other drugs.

All of these subpopulation effects could potentially be detected by doing clinical trials on more varied test populations. Since the relevant subpopulation will not, in general, be known ahead of time, the best approach is to create a representative diverse sample based on a large number of personal characteristics—genetic, physical, lifestyle, etc. OptiSim is ideally suited for defining an appropriate test group from such information since it allows intelligent choices to be made between the representativeness and diversity of the subsets of test populations to be chosen.

Internet Searching

The Internet represents an immense body of information which is expanding at a phenomenal rate. A major problem presented by so much readily accessible information is the ability to find the item(s) of interest. OptiSim may be applied to Internet searching to simplify the task of identifying relevant information. At present, such searches, of necessity, operate off a hierarchy of keywords and indices. Besides the shear volume of information which needs to be searched, this approach is susceptible to various abuses by Net publishers, some conscious and some accidental, as well as to the idiosyncracies of the various search engines and is prone to losing signal in the torrent of noise. As a result, users often have difficulty finding the information they seek. An alternative methodology enabled by Optisim would be to collect all addresses which might be relevant to the query, then use OptiSim to select diverse representatives and cluster the rest for perusal as appropriate. The user could by experience determine his/her personal value of K which most frequently returned information of most interest.

OptiSim is a generalized dissimilarity selection methodology which includes the established methods of maximum and minimum dissimilarity selection as special cases. By varying the subsample size K, one can adjust the balance between how representative the selected subset is and how diverse it is. Intermediate settings can mimic the results obtained for selection based on hierarchical clustering or, in some cases at least, improve upon them. Different embodiments of the invention disclosed in this document will consist of different datasets, different subset sizes, different dissimilarity measures, and different choices for the value of K. All are considered within the scope of the teaching of the Optisim invention. In addition, those skilled in the art will recognize that various modifications, additions substitutions, and variations to the illustrative examples set forth herein can be made without departing from the spirit of the inventions and are, therefore, considered within the scope of the invention.

REFERENCES

1. Barnard, J. M.; Downs, G. M. Clustering of chemical structures on the basis of two-dimensional similarity measures. *J. Chem. Inf. Comput. Sci.* 1992, 32, 644–649.
2. Lajiness, M.; Johnson, M. A.; Maggiora, G. M. Implementing drug screening programs using molecular similarity methods. In QSAR: *Quantitative Structure-Activity Relationships in Drug Design;* Fauchere, J. L., Ed.; Alan R. Liss, Inc.: New York, 1989; pp 173–176.
3. Holliday, J. D.; Willett, P. Definitions of "dissimilarity" for dissimilarity-based compound selection. *J. Biomol. Screening* 1996, 1, 145–151.
4. Agrafiotis, D. K. Stochastic algorithms for maximizing molecular diversity. *3rd Electronic Computational Chemistry Conference* 1996.
5. See, for example: Brannigan, L. H.; Duewer, D. L. Experimental design in the Development of biologically active compounds. *Pharmacochem. Libr.* 1991, 16, 553–556.
6. DiverseSolutions, from R. S. Pearlman (University of Texas at Austin) is available through Tripos, Inc., 1699 S. Hanley Road, St. Louis Mo. 63144.
7. Lance, G. N.; Williams, W. T. A. A general theory of classificatory sorting strategies. I. Hierarchical systems. *Comput. J.* 1967, 9, 373–380.
8. Murtagh, F. A survey of recent advances in hierarchical clustering algorithms. *Comput. J.* 1983, 26, 354–359.
9. Brown, R. D.; Martin, Y. C. Use of structure-activity data to compare structure-based clustering methods and descriptors for use in compound selection. *J. Chem. Inf. Comput. Sci.* 1996, 36, 572–584.
10. Patterson, D. E.; Cramer, R. D.; Ferguson, A. M.; Clark, R. D.; Weinberger, L. E. Neighborhood behavior: a useful concept for validation of molecular diversity descriptors. *J. Med. Chem.* 1996, 39, 3049–3059.
11. Holliday, J. D.; Ranade, S. S.; Willett, P. A fast algorithm for selecting sets of dissimilar molecules from large chemical databases. *Quant. Structure-Activity Rel.* 1996, 14, 501–506.
12. Patent pending.
13. Legion, SYBYL, UNITY and Selector are available from Tripos, Inc., 1699 S. Hanley Road, St. Louis Mo. 63144.
14. Gower, J. C. Measures of similarity, dissimilarity, and distance. In *Encyclopedia of Statistical Sciences;* Kotz, S., Johnson, N. L., Eds.; John Wiley & Sons, New York; 1985; Vol 5, p. 397–405.
15. Cheng, C.; Maggiora, G.; Lajiness, M.; Johnson, M. Four association coefficients for relating molecular similarity measures. J. Chem. Inf. Comput. Sci. 1996, 36, 909–915.
16. Conover, W. J. *Practical Non-parametric Statistics, 2nd Edition.* John Wiley & Sons, New York: 1980; p 143–170.
17. Mannhold, R.; Rekker, R. E.; Sonntag, C.; terLaak, A. M.; Dross, K.; Polymeropoulos, E. E. Comparative evaluation of the predictive power of calculation procedures for molecular lipophilicity. *J. Pharm. Sci.* 1995, 84, 1410–1419.
18. Mood, A. M.; Graybill, F. A.; Boes, D. C. *Introduction to the Theory of Statistics, 3rd Edition.* McGraw-Hill, New York; 1974; p. 232.
19. Molcrular Diversity Manager Manual, Version 6.3; Tripos, Inc., St. Louis: 1996; pp 212–213.
20. Kaufman, L.; Rousseeuw, P. J. In *Finding Group in Data: An Introduction to Cluster Analysis;* Wiley-Interscience, New York: 1990; p. 230.

What is claimed is:

1. A computer implemented method for selecting from the members of a population of N members, a member group, of predetermined size M, using predetermined characteristics representative of the members of the population and a dissimilarity measure R, said selected member group having a desired representativeness or diversity with respect to the members of the population comprising the following steps:

a) randomly select a member from the population, add it to the member group, create a pool of candidate members out of the remainder of the population, and create an empty recycling bin;

b) randomly choose a member from the pool of candidate members and determine if it has a dissimilarity less than R with respect to those members already selected for the member group, and, if it does not have a dissimilarity less than R, place it in a subpopulation;

c) if the member selected in step b has a dissimilarity less than R to those members already selected for the member group, discard that member;

d) repeat steps b and c until the subpopulation includes K members at least R dissimilar to those already selected for the member group or until the pool of candidate members is empty;

e) if the pool of candidate members is empty, and the recycling bin has members, remove all members from the recycling bin and put them into the pool of candidate members;

f) if the pool of candidate members is not empty, and, if there are fewer than K members in the subpopulation, go to step b;

g) if the subpopulation is empty, terminate the selection process;

h) if the subpopulation is not empty, examine the subpopulation and identify a member maximally dissimilar to those members already selected for the member group;

i) add the member identified in step h to the member group and remove it from the subpopulation;

j) put the members of the subpopulation, which were not added to the member group, into the recycling bin;

k) if the member group size equals predetermined size M, terminate the selection process; and l) if the member group size has not reached predetermined size M, return to step b wherein the value of K is selected to determine the representativeness or diversity desired in the member group of size M, provided that K≠1 and K≠N, and the value of R is selected to determine the minimum dissimilarity between members.

2. The method of claim 1 in which at step j, the members are not put into the recycling bin, but rather are immediately put back into the pool of candidate members.

3. The method of claim 1 in which the predetermined characteristic representative of the members of the population is chemical structure.

4. A computer implemented method for selecting from the members of a population of N members, a member group of predetermined size M, using predetermined characteristics representative of the members of the population and a preference criterion, said selected member group having a desired representativeness or diversity with respect to the members of the population comprising the following steps:

a) randomly select a member from the population and add it to the member group;

b) for each additional member to be included in the member group, randomly create a non-redundant subpopulation from the whole population;

c) select, using a preference criterion, the member from the subpopulation which best satisfies the preference criterion with respect to those members already selected for inclusion in the member group;

d) repeat steps a and b until M members are selected or until a non-redundant subpopulation can not be obtained.

5. The method of claim 4 in which the subpopulation size is varied to adjust the representativeness or diversity of the member group.

6. The method of claim 4 in which the predetermined characteristic representative of the members of the population is chemical structure.

7. A computer implemented method for selecting from the members of a population of N members, a member group of predetermined size M, using predetermined characteristics representative of the members of the population said selected member group having a desired representativeness or diversity with respect to the members of the population comprising drawing the members for testing for inclusion in the member group from a subpopulation the size of which is varied to balance the representativeness and diversity of the members selected.

8. The method of claim 7 in which the subpopulation is randomly selected and non-redundant.

9. The method of claim 7 in which the testing of the members for inclusion in the member group comprises satisfying a preference criterion.

10. The method of claim 7 utilizing subpopulations of size K, where $K \neq 1$ and $K \neq N$, in which the number of iterations for selecting the group is less than or equal to the population size and typically approximates the square root of the population size.

11. The method of claim 7 in which the predetermined characteristic representative of the members of the population is chemical structure.

12. An iterative computer implemented method for selecting from the members of a population of N members, a member group of predetermined size M, using predetermined characteristics representative of the members of the population said selected member group having a desired representativeness or diversity with respect to the members of the population comprising selecting subpopulations of size K from which the members are drawn, where $K \neq 1$ and $K \neq N$, in which the number of iterations for selecting the member group of size M is less than or equal to the population size and typically approximates the square root of the population size.

13. The method of claim 12 in which the predetermined characteristic representative of the members of the population is chemical structure.

14. A computer implemented method for clustering members of a large population of N members, using predetermined characteristics representative of the members of the population and a dissimilarity measure R, the clusters having a desired representativeness or diversity with respect to the members of the population in which the center of the clusters to be formed are determined by the member groups selected from the population by the method comprising the following steps:

a) randomly select a member from the population, add it to the member group, create a pool of candidate members out of the remainder of the population, and create an empty recycling bin;

b) randomly choose a member from the pool of candidate members and determine if the member has a dissimilarity less than R with respect to those members already selected for the member group, and, if the member does not have a dissimilarity less than R, place the member in a subpopulation;

c) if the member selected in step b has a dissimilarity less than R to those members already selected for the member group, discard that member;

d) repeat steps b and c until the subpopulation includes K members at least R dissimilar to those already selected for the member group or until the pool of candidate members is empty;

e) if the pool of candidate members is empty, and the recycling bin has members, remove all members from the recycling bin and put them into the pool of candidate members;

f) if the pool of candidate members is not empty, and, if there are fewer than K members in the subpopulation, go to step b;

g) if the subpopulation is empty, terminate the selection process;

h) if the subpopulation is not empty, examine the subpopulation and identify a member maximally dissimilar to those members already selected for the member group;

i) add the member identified in step h to the member group and remove it from the subpopulation;

j) put those members in the subpopulation, which were not added to the member group, into the recycling bin; and k) if the member group size M has been reached, terminate the selection process;

l) if the member group size M has not been reached, return to step b wherein the value of K is selected to determine the representativeness or diversity desired in the group, provided that $K \neq 1$ and $K \neq N$, and the value of R is selected to determine the minimum dissimilarity between members.

15. The method of claim 14 in which the predetermined characteristic representative of the members of the population is chemical structure.

16. A computer implemented method for clustering members of a large population of N members, using predetermined characteristics representative of the members of the population, in which the center of the clusters to be formed are determined by member groups selected from the population by the method comprising the following steps:

a) randomly select a member from the population and add it to a member group;

b) for each additional member to be included in the member group, randomly create a non-redundant subpopulation from the whole population;

c) select, using a preference criterion, the member from the subpopulation which best satisfies the preference criterion with respect to those members already selected for inclusion in the member group;

d) repeat steps a and b until M members are selected or until a non-redundant subpopulation can not be obtained.

17. The method of claim 16 which the predetermined characteristic representative of the members of the population is chemical structure.

* * * * *